(12) United States Patent  (10) Patent No.: US 7,855,077 B2
Wilson  (45) Date of Patent: Dec. 21, 2010

(54) METHOD AND DEVICE FOR TEST SAMPLE LOADING

(75) Inventor: Brian D. Wilson, Chaska, MN (US)

(73) Assignee: Beckman Coulter, Inc., Brea, CA (US)

( * ) Notice: Subject to any disclaimer, the term of this patent is extended or adjusted under 35 U.S.C. 154(b) by 42 days.

(21) Appl. No.: 11/540,227

(22) Filed: Sep. 29, 2006

(65) Prior Publication Data
US 2009/0035866 A1   Feb. 5, 2009

(51) Int. Cl.
  *G01N 35/02*  (2006.01)
  *G01N 35/04*  (2006.01)
(52) U.S. Cl. .............. 436/47; 436/43; 436/48; 436/49; 436/180; 422/63; 422/65; 422/100
(58) Field of Classification Search ............ None
  See application file for complete search history.

(56) References Cited
U.S. PATENT DOCUMENTS

| | | | |
|---|---|---|---|
| 5,587,129 A | 12/1996 | Kurosaki et al. | |
| 5,885,530 A | 3/1999 | Babson et al. | |
| 6,776,961 B2 | 8/2004 | Lindsey et al. | |
| 6,790,412 B2 | 9/2004 | Willenbring et al. | |
| 6,790,413 B2 | 9/2004 | Ngo et al. | |
| 6,793,888 B2 | 9/2004 | Qureshi et al. | |
| 6,825,041 B2 | 11/2004 | Qureshi et al. | |
| 2002/0041829 A1* | 4/2002 | Kowallis | 422/63 |
| 2002/0102736 A1 | 8/2002 | Kittock et al. | |
| 2002/0131895 A1 | 9/2002 | Gjerdingen et al. | |

\* cited by examiner

*Primary Examiner*—P. Kathryn Wright
(74) *Attorney, Agent, or Firm*—Townsend and Townsend and Crew LLP

(57) ABSTRACT

An automated analyzer is configured to receive and analyze samples provided to the automated analyzer in primary sample containers. The automated analyzer comprises a sample retention unit, at least one transport device, and at least one aspiration device. The sample retention unit is configured to receive and retain a plurality of sample retention vessels. The sample retention unit may comprise a sample storage unit, an analytic unit, or other processing unit within the automated analyzer that retains a sample for some purpose. The transport device is configured to receive a first primary sample container containing a first sample and deliver the first primary sample container to the sample retention unit as one of the plurality of sample retention vessels. The aspiration device is configured to receive a second sample from a second primary sample container and deliver the second sample into one of the plurality of sample retention vessels.

16 Claims, 9 Drawing Sheets

METHOD AND DEVICE FOR TEST SAMPLE LOADING

FIELD

This disclosure relates to the field of automated chemical analyzers and related sample handling mechanisms.

BACKGROUND

Automated analyzers, including automated chemical analyzers and automated immunodiagnostic instruments are widely used in clinical chemistry sampling and analyzing applications. When using these analyzers, samples are loaded into the device at a sample presentation unit (i.e., a loading area) in primary sample containers. Primary sample containers may take various forms, but one typical primary sample container is a blood tube, such as the tube 24 shown in FIG. 9. These tubes may be loaded into the automated analyzer individually or in racks capable of holding multiple tubes.

After being loaded into the automated analyzer, a sample is typically aspirated from its primary sample container and dispensed into one or more sample retention vessels for aliquot storage. For example, in a typical automated analyzer, the samples delivered to the sample retention containers are stored in a chilled storage unit.

When the analytic unit of the automated analyzer is ready to analyze a sample, the diagnostic instrumentation typically aspirates from the aliquot and dispenses into a reaction vessel, and the analytic unit performs an analysis of the sample within the reaction vessel. Alternatively, in certain automated analyzers and in certain situations, the diagnostic instrumentation may be further configured to transfer the actual sample retention vessel from the storage area to analytic unit. Accordingly, the sample retention vessel serves as the reaction vessel in these situations.

In the above-described analyzers, there is an original transfer of sample from the primary sample container to the sample retention vessels in order to store the sample. Because of this original sample transfer, there is an unusable amount of fluid left in the primary sample container (also referred to as "dead volume"). In particular, the pipettor aspirating the sample can not draw the entire volume of fluid from the primary sample container, so some sample is wasted when a primary container with dead volume is expelled from the analyzer. In addition, each time sample is transferred from one container to another, dead volume results, minimizing the amount of available sample. Many samples presented to the automated analyzer have a very limited amount of fluid to start with, so minimization of the dead volume is desired, especially when multiple tests are to be conducted. An example of a situation where only a small amount of sample may be available is a blood sample from a pediatric patient where each drop of sample is difficult and painful to obtain. Accordingly, it would be advantageous to provide a chemical analyzer capable of minimizing the number of sample transfers, thus reducing the amount of dead volume for a given sample.

Another reason to reduce the number of sample transfers in an automated analyzer relates to sample carryover. In particular, when analyzing a given sample it is important that the sample remains pure, and that no residual materials from a prior sample are introduced into a subsequent sample. The primary methods to address sample carryover include washing of the pipettor probe and the use of disposable pipette tips. While these methods significantly reduce sample carryover, they do not completely remove all chances of sample carryover. However, if the automated analyzer could be operated with fewer sample transfers, the chances for sample carryover can be further reduced.

While an exemplary primary collection tube is shown in FIG. 9, not all primary sample containers holding original samples are identical. The primary sample containers may have differing shapes and sizes. In addition, some containers may be covered and some may be uncovered. As set forth above, transferring samples from one container to another is typically undesirable. Therefore, it would be advantageous to provide an automated analyzer capable of processing numerous shapes and sizes of primary sample containers. It would also be advantageous if the analyzer were configured to handle both covered and uncovered containers.

Medical professionals rely on automated analyzers to perform multiple tests on multiple samples within a relatively short amount of time. When some portion of an automated analyzer is not working, important test results may be delayed. Thus it would be advantageous to provide an automated analyzer having some redundant capabilities such that samples may be still processed even if one portion of the automated analyzer is inoperable.

Medical professionals also rely on automated analyzers to perform differing tests on different samples. Often, a medical professional may wish to process and/or analyze a first sample in one way and a second sample in a different way. Therefore, it would be advantageous to provide an automated analyzer having multiple options for sample processing. It would also be advantageous if the automated analyzer were configured for connection to another analyzer such that samples could be shared between the analyzer, thus offering the medical professional additional options for processing and analysis.

SUMMARY

An automated analyzer is disclosed herein. The automated analyzer is configured to receive and analyze samples provided to the automated analyzer in primary sample containers. The automated analyzer comprises a sample retention unit, at least one transport device, and at least one aspiration device.

The sample retention unit of the automated analyzer is configured to receive and retain a plurality of sample retention vessels. The sample retention unit may comprise a sample storage unit, an analytic unit, or other processing unit within the automated analyzer that retains a sample for some purpose over some period of time.

The transport device of the automated analyzer is configured to receive a first primary sample container containing a first sample and deliver the first primary sample container to the sample retention unit as one of the plurality of sample retention vessels. In one embodiment, the transport device comprises a pick-and-place device configured to grasp the first primary sample container and move it to the sample retention unit for further processing.

The aspiration device of the automated analyzer is configured to receive a second sample from a second primary sample container and deliver the second sample into one of the plurality of sample retention vessels. In one embodiment, the aspiration device comprises a pipettor configured to draw the second sample from the second primary sample container and dispense the sample into one or more sample retention vessels.

In addition to the above, the automated analyzer may comprise a sample presentation unit configured to receive the primary sample containers and automatically deliver the primary sample containers to a transfer station within the automated analyzer. The transfer station provides an area where a primary sample container may be handled by the transport device or sample within a primary sample container may be aspirated by the aspiration device. Both the aspiration device and the transfer device may be provided on a dual gantry robot which includes a first carriage supporting the aspiration device and a second carriage supporting the transport device.

The automated analyzer may further comprise a second transport device configured to receive primary sample containers from and deliver primary sample containers to the first transport device. Accordingly, the second transport device may be configured to transfer primary sample containers to and from a laboratory instrument housed separate from the automated analyzer.

In one embodiment, the automated analyzer further comprises an analytic unit configured to analyze the samples in the sample retention vessels. The analytic unit may include a plurality of reagent pipetting stations configured to transfer the samples from the sample retention vessels and into reaction vessels and mix reagents with the samples.

The disclosed automated analyzer provides for a method of preparing samples for analysis. The method comprises first loading a plurality of primary sample containers into an automated analyzer that includes a sample retention unit configured to receive a plurality of sample retention vessels. The sample retention unit may be a sample storage unit, an analytic unit, or other processing unit within the automated analyzer that retains a sample for some period of time. A sample is retained within each of the plurality of primary sample containers that are loaded into the automated analyzer. After a first primary sample container of the plurality of primary sample containers is loaded on the automated analyzer, the first primary sample container is transferred into the sample retention unit as one of the plurality of sample retention vessels. After a second primary sample container is loaded on the automated analyzer, the sample in the second primary sample container is transferred into at least one of the plurality of sample retention vessels in the sample retention unit. Thereafter, the sample in the first primary sample container and the sample transferred from the second primary sample container are analyzed or otherwise processed within the automated analyzer.

In one disclosed embodiment, the above method includes manually loading the plurality of primary sample containers into a sample presentation unit and automatically delivering the plurality of primary sample containers to a transfer station within the automated analyzer. The step of transferring the first primary sample container to the sample retention unit and the step of transferring the sample from the second primary sample container to the sample retention unit are performed at the transfer station within the automated analyzer.

In another disclosed embodiment, the method step of loading the plurality of primary sample containers into the automated analyzer comprises receiving at least some of the plurality of primary sample containers from a laboratory instrument housed separate from the automated analyzer.

The above described features and advantages, as well as others, will become more readily apparent to those of ordinary skill in the art by reference to the following detailed description and accompanying drawings.

DESCRIPTION

Figure 1:
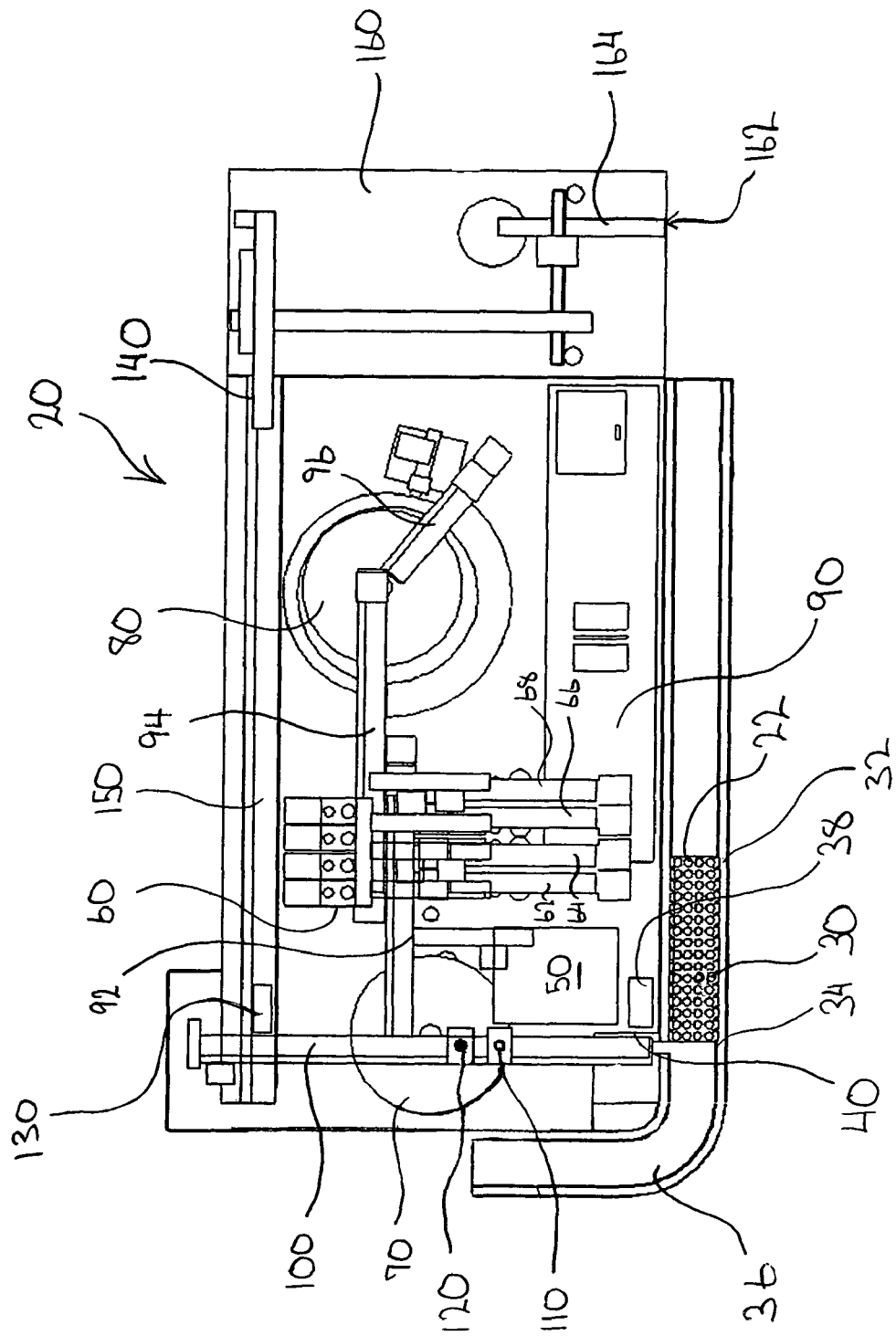
FIG. 1 shows a plan view of the modules of an automated analyzer.

As shown in FIG. 1, the basic structural and functional modules of one embodiment of an automated analyzer 20 include a sample presentation unit 30, a transfer station 40, a vessel feeder 50, an analytic unit 60, a sample aliquot storage unit 70, an incubator/wash/read station 80, and a reagent storage 90. In addition, the automated analyzer 20 includes an aspiration device 110 and a first transport device 120 in communication with the transfer station 40. The aspiration device 110 and the first transport device 120 are both provided on a gantry robot 100. A second transport device 150 is also provided in communication with the first transport device 100. An additional laboratory instrument 160 housed separate from the automated analyzer may be connected to the automated analyzer and configured to receive and deliver primary sample containers to the instrument.

General Structure of Automated Analyzer

Figure 9:
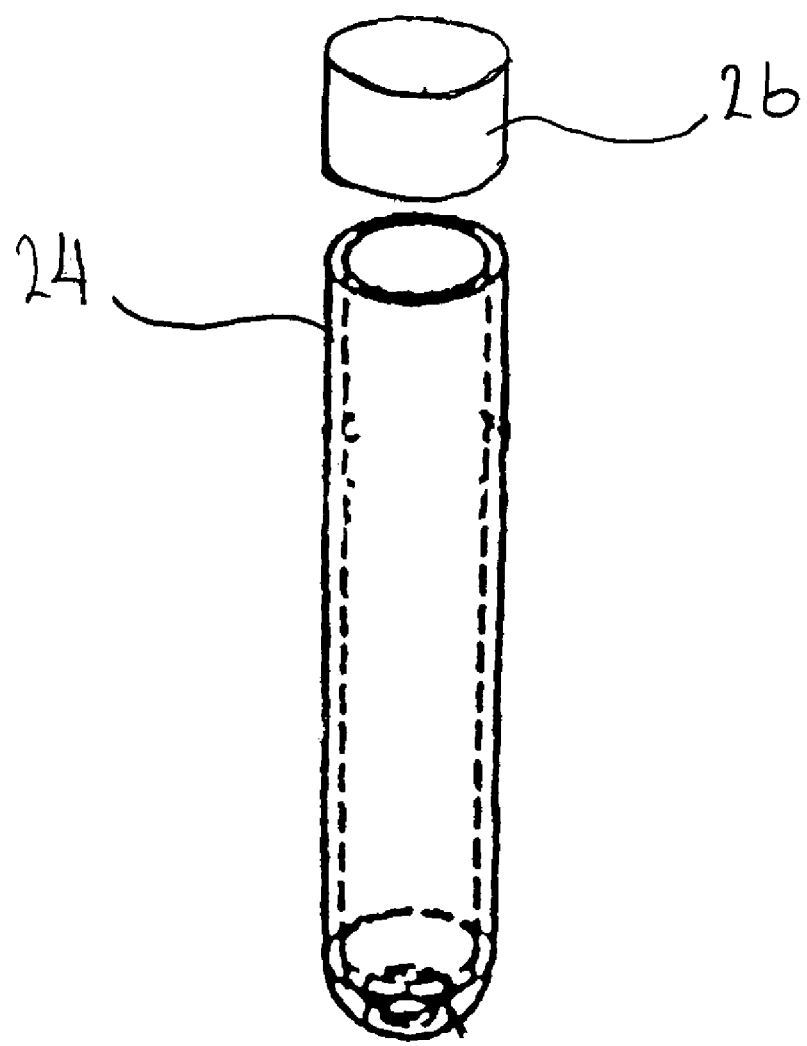
FIG. 9 shows an exemplary blood tube that may be used as a primary sample container in the automated analyzer of FIG. 1.

In the embodiment of FIG. 1, the sample presentation unit 30 is used to load primary sample containers 22 into the automated analyzer 20 and to the transfer station 40. As used herein, the term "primary sample container" refers to a container that is loaded into the automated analyzer with a sample contained therein. Primary sample containers may include, for example, blood tubes where blood is initially placed after being drawn from a patient's body. Such an exemplary primary sample container 22 is shown in FIG. 9 in the form of a blood tube 24. The blood tube 24 may be configured for seating in a tube rack (not shown). A cap, cork, plug or other top 26 may be placed on the tube 24 to prevent spillage or contamination of the sample within the tube.

With reference again to FIG. 1, the sample presentation unit 30 includes an onload section 32, a presentation section 34, and an offload section 36. The primary sample containers 22 are manually placed into the onload section 32, either individually or in racks. After being placed in the onload section, the primary sample containers 22 are automatically pushed to the presentation section 34 of the sample presentation unit. At the presentation section 34, the primary sample containers 22 are automatically fed to the transfer station 40 located within the housing of the automated analyzer 20. When a primary sample container 22 passes into the housing, a bar code reader 38 reads a bar code associated with the primary sample container, such as a bar code affixed to the side of the container. The bar code identifies how the primary sample container 22 and its sample should be processed within the automated analyzer. After a primary sample container is processed within the automated analyzer 20, the primary sample container 22 is typically discarded. However, in some situations, the processed primary sample container may be delivered to an offload station 36, where the primary sample container may be manually removed from the automated analyzer. Sample presentation units 30 for automated analyzers, such as that described above, are generally known to those of skill in the art. For example, one embodiment of a sample presentation unit 40 is described in U.S. Pat. No. 6,790,413, which is incorporated herein by reference in its entirety. However, it should be understood that other lab automation systems or automated track conveyance systems may also used to load primary sample containers and racks holding primary sample containers into the automated analyzer 20.

The transfer station 40 receives primary sample containers 22 from the sample presentation unit 30. Accordingly, the transfer station 40 includes a staging area which may include one or more seats configured to receive primary sample containers or racks holding the primary sample containers. Primary sample containers 22 delivered to the transfer station 40 may be initially processed in different ways. For example, upon arrival at the transfer station 40, a primary sample container 22 may be handled by the first transport device 120 and delivered to another location within the automated analyzer 20. Alternatively, the primary sample container may temporarily remain at the transfer station while the sample provided within the primary sample Container is aspirated by the aspiration device 110 at the transfer station. Following such aspiration, the primary sample container 22 may be expelled from the automated analyzer at the offload station, or may be passed on to the first transport device 120 for further processing.

As set forth in the preceding paragraph, both the transport device 120 and the aspiration device 110 are configured to interact with primary sample containers at the transfer station 40. As explained in further detail below, both the first aspiration device 110 and the first transport device 120 may be provided on a gantry robot 100. The gantry robot 100 is configured to selectively move either the aspiration device 110 or the transport device 120 to and from the transfer station 40.

With continued reference to FIG. 1, the vessel feeder 50 of the automated analyzer 20 is generally configured to receive sample retention vessels and provide the sample retention vessels to one or more sample retention units. As used herein, the term "sample retention vessel" refers to a tube or other vessel that is configured to be retained by one of the sample retention units of the automated analyzer. The term "sample retention unit" refers to a device, station or other unit of the automated analyzer configured to receive sample retention vessels and store, analyze, or otherwise process samples retained within the sample retention vessels. For example, in the example of FIG. 1, both the analytic unit 60 and the sample storage unit 70, as well as other units, may be considered sample retention units. One of skill in the art will recognize that sample retention vessels may take numerous forms and configurations. For example, sample retention units may comprise aliquot tubes as well as blood tubes, such as the blood tube 24 shown in FIG. 9. Furthermore, it should be recognized that a "primary sample container" loaded into the automated analyzer with a sample may also be considered a "sample retention vessel" when placed in a sample retention unit, such as the storage unit 70.

The vessel feeder 50 is configured to provide sample retention vessels to sample retention units within the automated analyzer, such as the sample storage unit 70 or the analytic unit 60. The vessels provided by the vessel feeder are typically empty vessels held in bulk by the vessel feeder 50. Vessel feeders are generally known to those of skill in the art. A description of the configurations and functions of an exemplary vessel feeder 50 is provided in U.S. Pat. No. 6,790,412, which is incorporated herein by reference in its entirety. However, it should be understood that other vessel supply mechanisms capable of supplying sample vessels are also suitable for use with the disclosed embodiment of the automated analyzer 20.

The analytic unit 60 shown in FIG. 1 is configured to receive and analyze samples. In the disclosed embodiment, the analytic unit 60 includes four reagent pipetting stations 62, 64, 66, and 68, used to mix reagents with sample aliquots from sample retention vessels for subsequent assay. A sample aliquot may be transferred from the sample retention vessels into one or more vessels referred to as "reaction vessels" in order to mix the sample aliquot with one or more reagents. In some cases, a sample aliquot may also be transferred from the sample retention vessel to a reaction vessel without mixing the aliquot with reagents. The pipetting stations 62, 64, 66, and 68 are independent to each other, each having its own fluid pumps and valves, wash towers, reaction vessel carriages, and pipettor. The reagent pipetting stations have access to reagents that are stored in reagent storage 90. The individual structures and functions of the reagent pipetting stations 62, 64, 66, and 68 are generally known to those of skill in the art. For example, the reagent pipetting stations used in the Access Instruments sold by Beckman Coulter, Inc., of California.

Testing of samples within the sample retention vessels may occur at various modules within the analytic unit 60, the incubator/wash/read station 80 or elsewhere within the automated analyzer. In some instances, testing of samples within sample retention vessels may occur within off-board instruments connected to the automated analyzer 20. Exemplary instruments configured to test samples include clinical chemistry systems, immunoassay systems, flow cytometers, and hematology analyzers. However, one of skill in the art will recognize that numerous other instruments may be used to perform testing and analysis of samples within the sample retention devices.

The sample storage unit 70, as shown in FIG. 1, is used for storing sample aliquots contained in the sample retention vessels. In particular, the sample storage unit 70 is configured to store sample aliquots in a controlled environment enclosure at a low temperature for a certain period of time, so that the samples may be used for analysis and testing. When a test is requested on a patient sample, the test outcome may drive a request for additional testing. This automatic request for additional tests is reflex testing. The time delay from the first aspiration to knowing if another test will be started can range to as long as 45 minutes or more. To insure that the test materials do not evaporate or deteriorate, the sample aliquots are enclosed and refrigerated in the sample storage unit 70.

Figure 7:
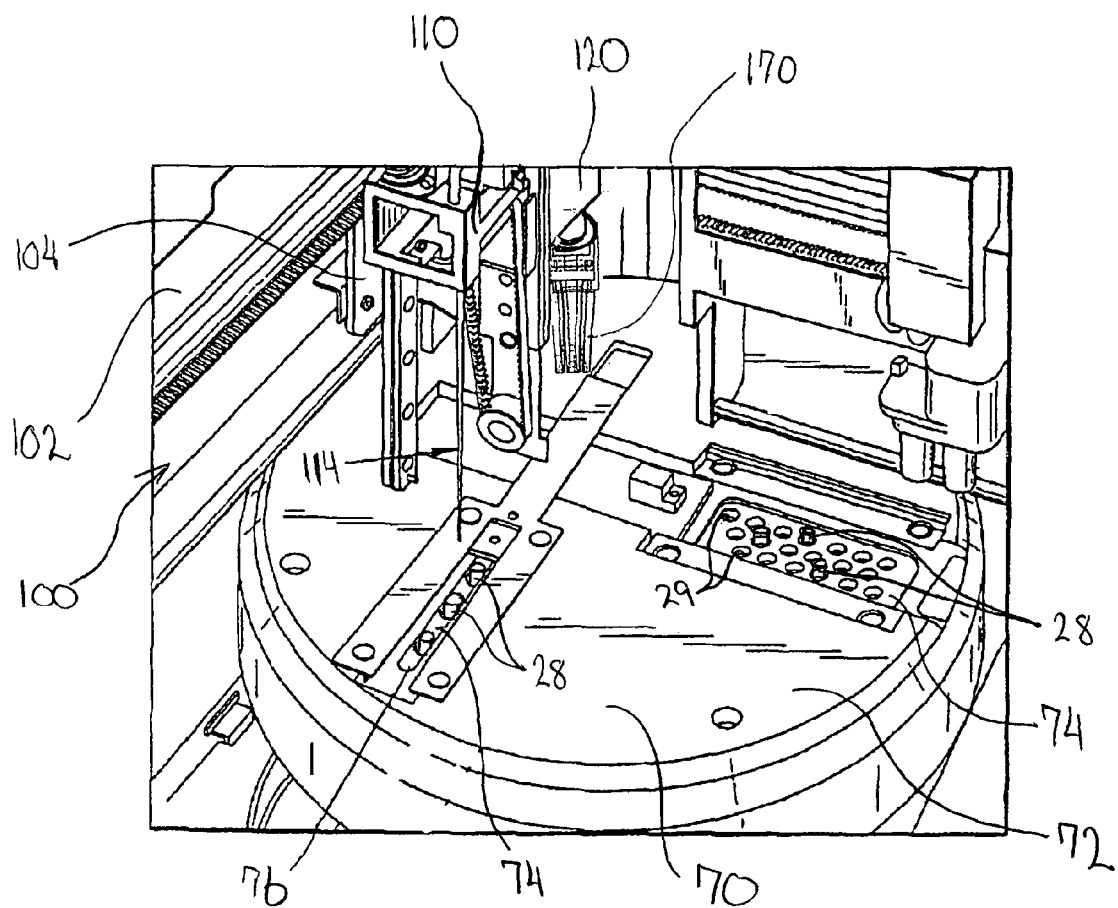
FIG. 7 shows a perspective view of the aspiration device and the transport device positioned over the storage unit of FIG. 2.

As can be seen in FIG. 7, the sample storage unit 70 generally comprises an outer housing 72 and an inner wheel 74. At least one slot 76 is provided in the outer housing 72 to provide access to the inner wheel 74. The inner wheel 74 includes a circular plate with a plurality of holes 29 that provide seats for sample retention vessels 28. The inner wheel 74 is configured to rotate within the outer housing 72, allowing each individual sample retention vessel 28 retained within the sample storage unit 70 to be presented to the slot 76.

Returning again to FIG. 1, the automated analyzer 20 also comprises a plurality of vessel transport devices, such as transport devices 92, 94, and 96, which are used to transport sample retention vessels among the various modules and sample retention units of the automated analyzer 20. Each vessel transport device 92, 94, 96 may be provided by a pick-and-place device. Each pick-and-place device generally comprises a gripper assembly provided on a gantry robot capable of moving the gripper assembly along at least two axes.

Figure 8:
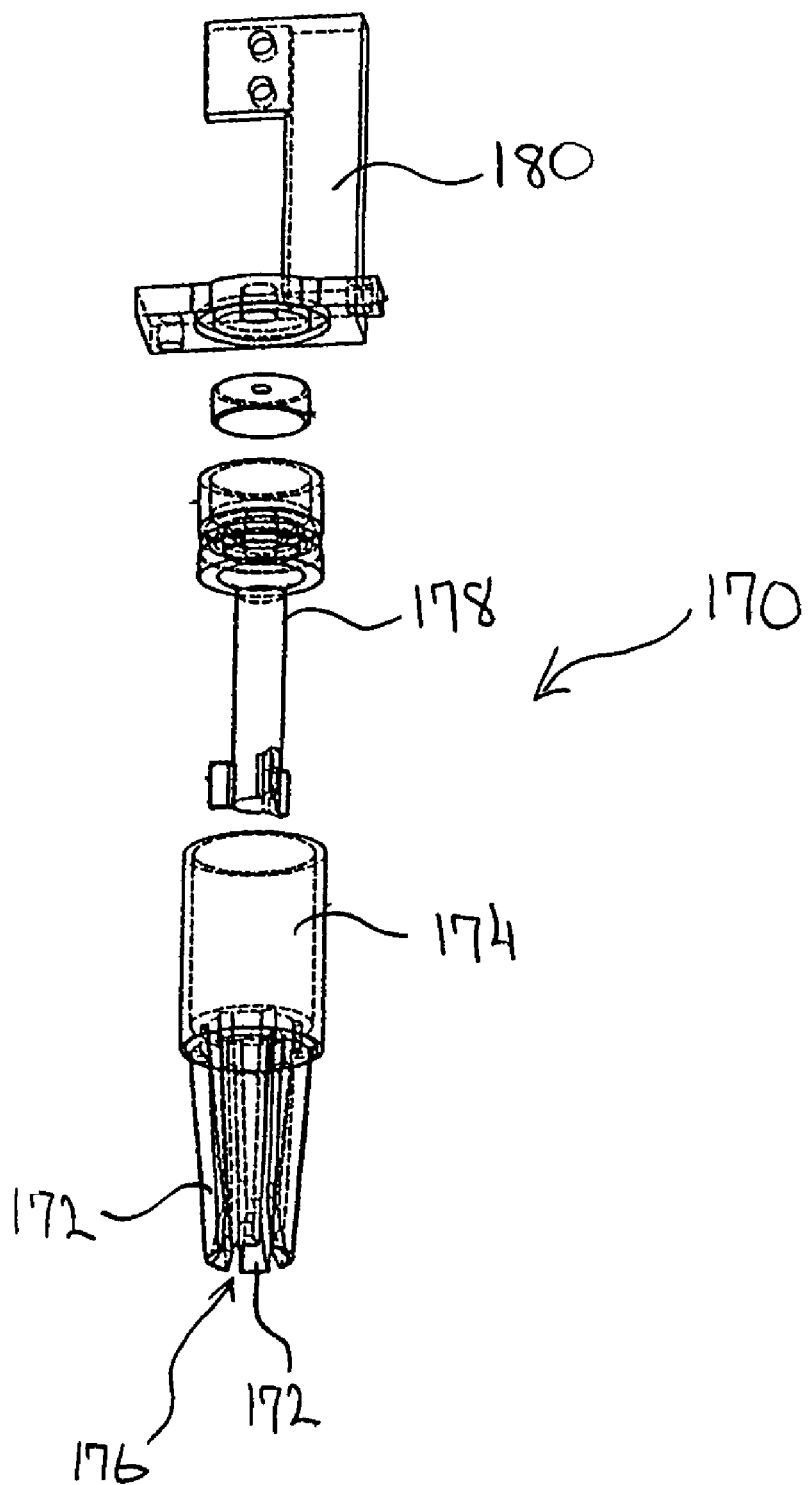
FIG. 8 shows a gripper assembly of a pick-and-place device of the automated analyzer of FIG. 1.

An exemplary gripper assembly 170 is shown in FIG. 8. The gripper assembly 170 includes an elongated body with a plurality of flexible adjustable fingers 172 connected to a cylinder 174 in a spaced apart relationship. The bottom ends of the fingers 172 form a slotted circular opening 176 adapted to receive a vessel. The cylinder 174 is held by a clamp 180 which, in turn, is connected to a carriage riding upon a gantry robot (not shown in FIG. 8). A plunger 178 moves within the cylinder and acts to open and close the opening 176, allowing the fingers 172 to selectively grasp and release vessels. Pick-and-place devices such as this are generally known to those of skill in the art. An exemplary pick and place device is disclosed in U.S. Patent Publication No. 2002/0102736, which is incorporated by reference herein in its entirety. However, it should be understood that other pick-and-place devices capable of transporting sample retention vessels and sample reaction vessels may be used with the disclosed embodiment of the automated analyzer.

As shown by the arrangement of FIG. 1, the first pick-and-place device 92 is used to transport sample retention vessels from the vessel feeder 50 to the sample storage unit 70 or the analytic unit 60 and its pipetting stations 62, 64, 66 and 68. The second pick-and-place device 94 is used to transport reaction vessels between the analytic unit 60 and the incubator of the incubator/wash/read station 80. The third pick-and-place device 96 is used to transport reaction vessels between the incubator wheel and the wash wheel of the incubator/wash/read station 80.

Processing of Primary Sample Containers

Figure 2:
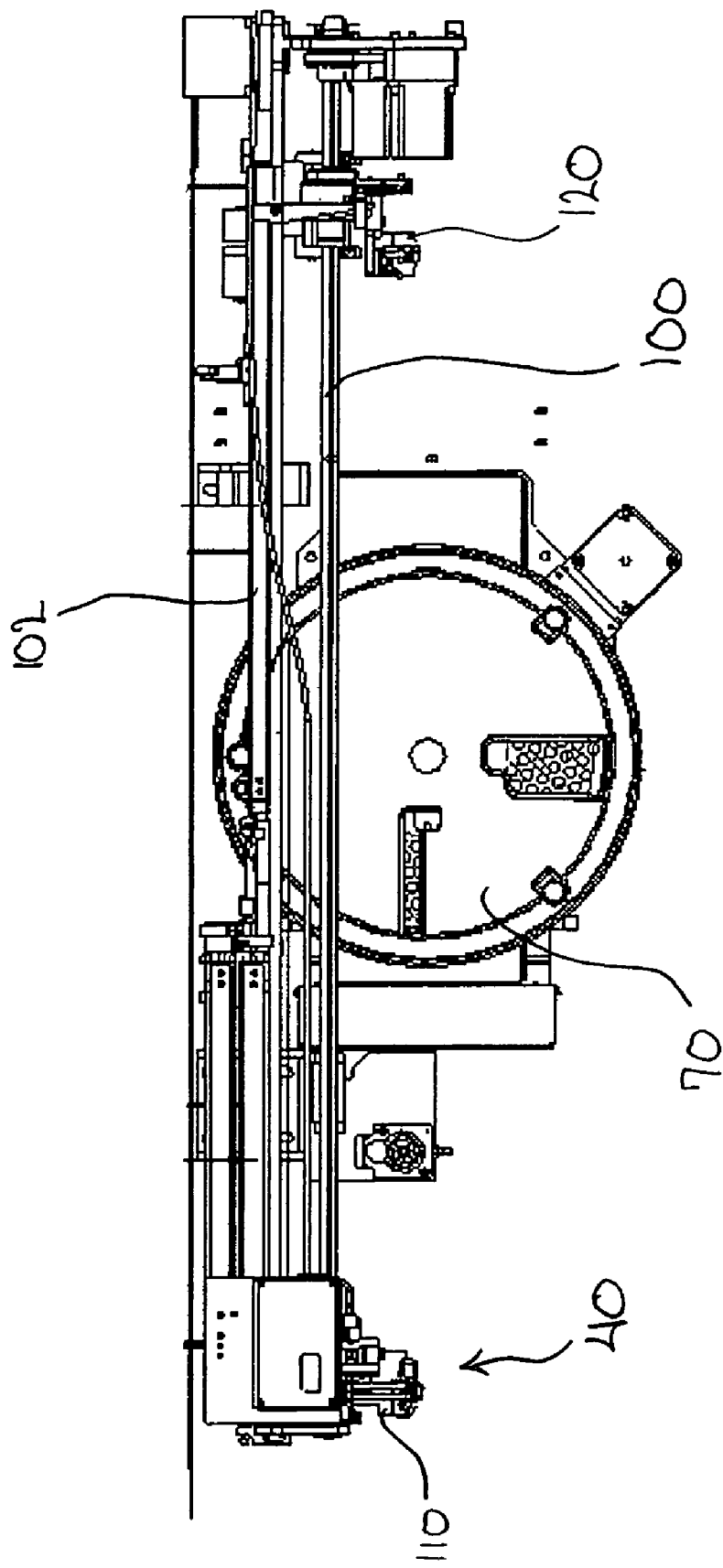
FIG. 2 shows a top view of an aspiration device and transport device provided on a gantry robot of the automated analyzer of FIG. 1, with a storage unit positioned under the gantry robot.
Figure 3:
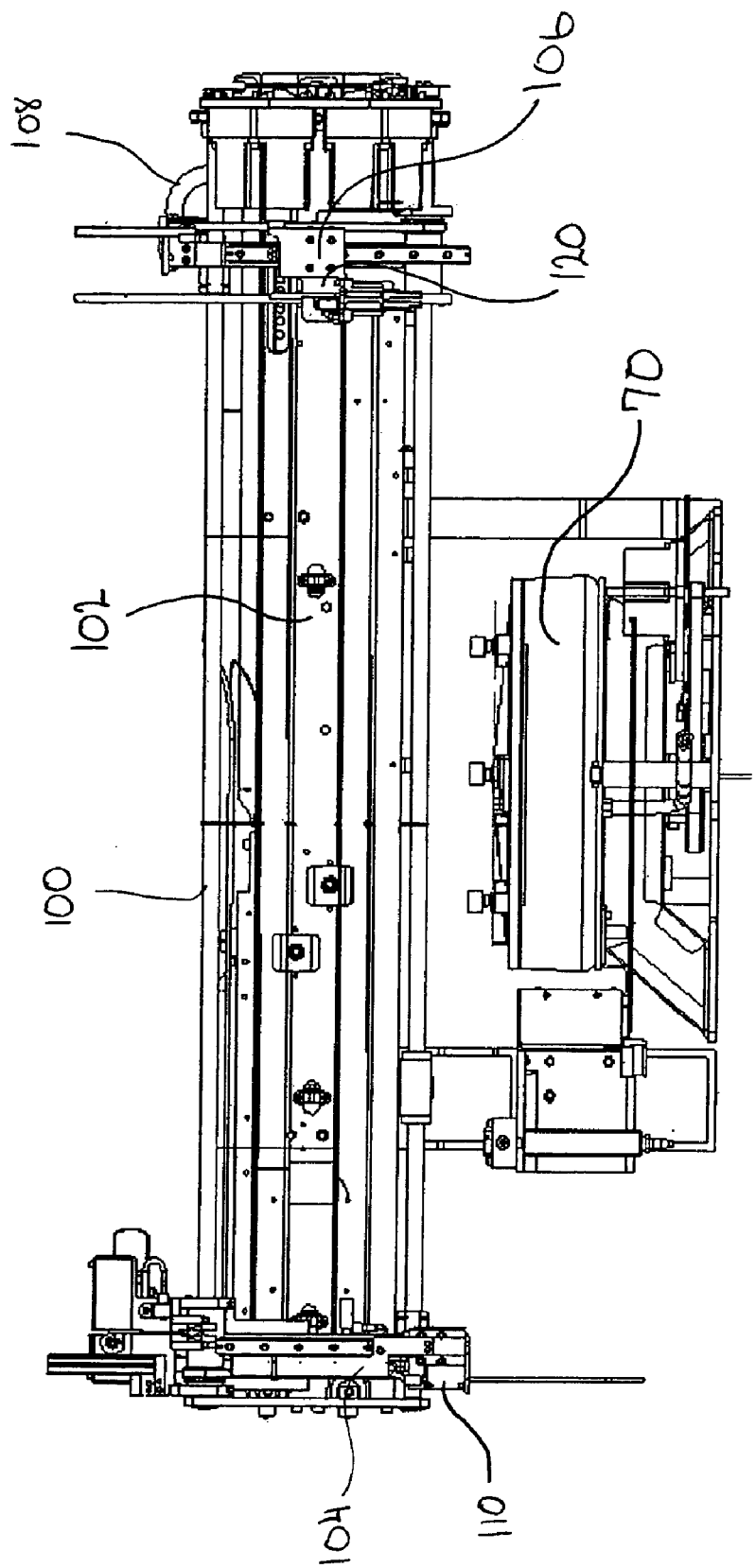
FIG. 3 shows a side view of the aspiration device and transport device of FIG. 2.

As mentioned above, both the aspiration device 110 and the first transport device 120 are configured to interact with primary sample containers at the transfer station 40. With reference now to FIGS. 2 and 3, it can be seen that the first aspiration device 110 and the first transport device 120 are provided on a gantry robot 100.

The gantry robot 100 is a Cartesian coordinate robot capable of moving a robotic member along at least two axes. In the embodiment shown in FIGS. 2 and 3, the gantry robot 100 includes a horizontal support 102 member that provides a track that defines a horizontal linear path of movement for the robot. A first carriage 104 and a second carriage 106 both ride upon the track. The first carriage 104 supports the aspiration device 110 and the second carriage 106 supports the transport device 120. Each carriage, 104, 106 can move from end to end of the horizontal support member, thus positioning the aspiration device 110 or the transport device 102 at any location along the horizontal support 102, including above the transfer station 40 near the front of the horizontal support member, above the sample storage unit 70 near the middle of the horizontal support member, or above an additional transport device near the rear of the horizontal support member. Drive mechanisms are provided to separately move the first carriage 104 and the second carriage 106 upon the horizontal track with each carriage moving independent of the other carriage. Such drive mechanisms for gantry robot are known and will be recognized by those of ordinary skill in the art.

A flexible connector member 108 is connected between the horizontal support 102 and each carriage 104, 106. The flexible connector members 108 retain conductors configured to deliver electrical power and/or signals between electronic components provided on the horizontal support 102 and the carriages 104, 106. These electrical conductors 108 are joined to other electrical conductors and related electrical components housed in control box for the gantry robot. For example, a microprocessor configured to deliver drive control signals, aspirator control signals, and transport device control signals may be housed in the control box.

Each carriage 104, 106 includes a member that engages the track on the horizontal support 102 and a vertical arm that defines movement of an attached component in the vertical direction. Thus, the first carriage 104 includes a vertical arm 105 that defines movement the aspiration device 110 in a vertical direction. Likewise, the second carriage 106 includes a vertical arm 107 that provides for movement of the transport device 120 in the vertical direction. Therefore, in addition to moving to any position along the horizontal support member 102, the aspiration device 110 and the transport device 120 may also move up and down along a vertical linear path of movement. Accordingly, each carriage 104, 106 is provided with a drive mechanism that engages the vertical arm and moves it up and down. Robotic arm and drive train arrangements configured to move devices up and down on gantry robots are known and will be recognized by those of ordinary skill in the art.

Figure 4:
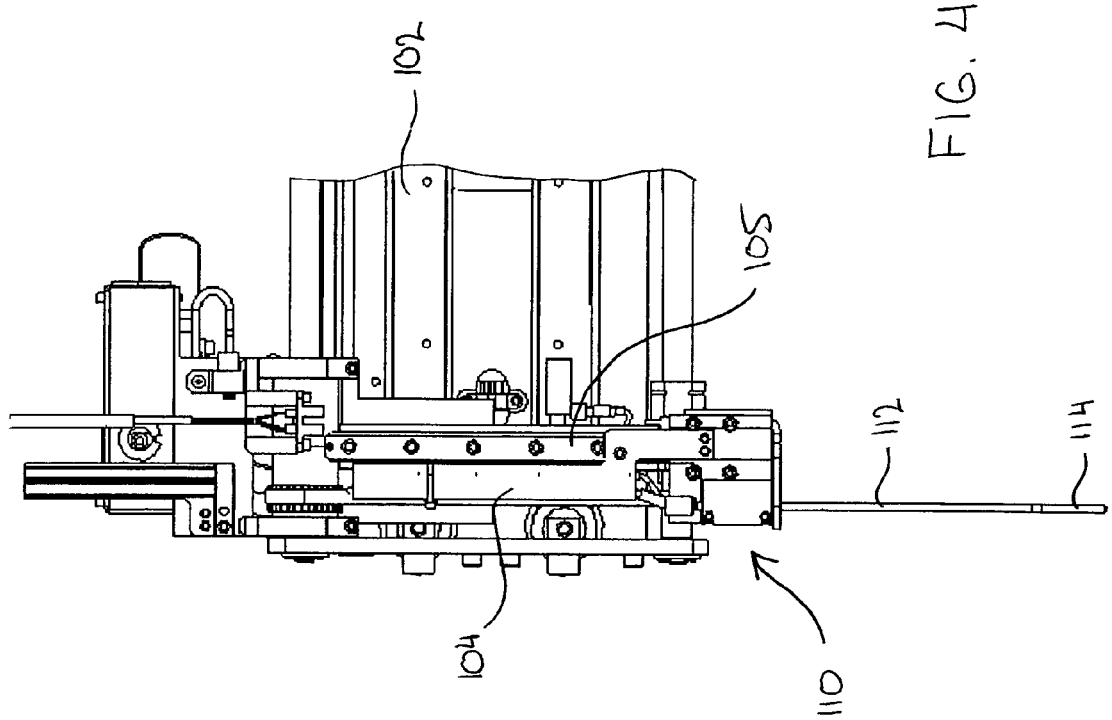
FIG. 4 shows an enlarged side view of the aspiration device of FIG. 3.

With reference now to FIG. 4, the aspiration device 110 is shown upon an end of the horizontal support 102 of the gantry robot 100. The aspiration device is a pipettor assembly that includes a mandrel 112 with a hole in the end. When a vacuum of the pipettor assembly is applied to the mandrel, air is drawn into the mandrel 112. A pipette tip 114 is typically provided at the end of the mandrel 112. The pipette tip 114 is the portion of the pipettor that actually contacts the fluid to be aspirated. The pipette tips 114 are washable or disposable and are replaced between pipetting operations to reduce the risk of contamination of the samples and reagents engaged by the pipettor. Pipettors, such as the exemplary pipettor shown in FIG. 4, are well known to those of ordinary skill in the art, along with their construction and operation in relation to gantry robots for automated laboratory devices.

Figure 5:
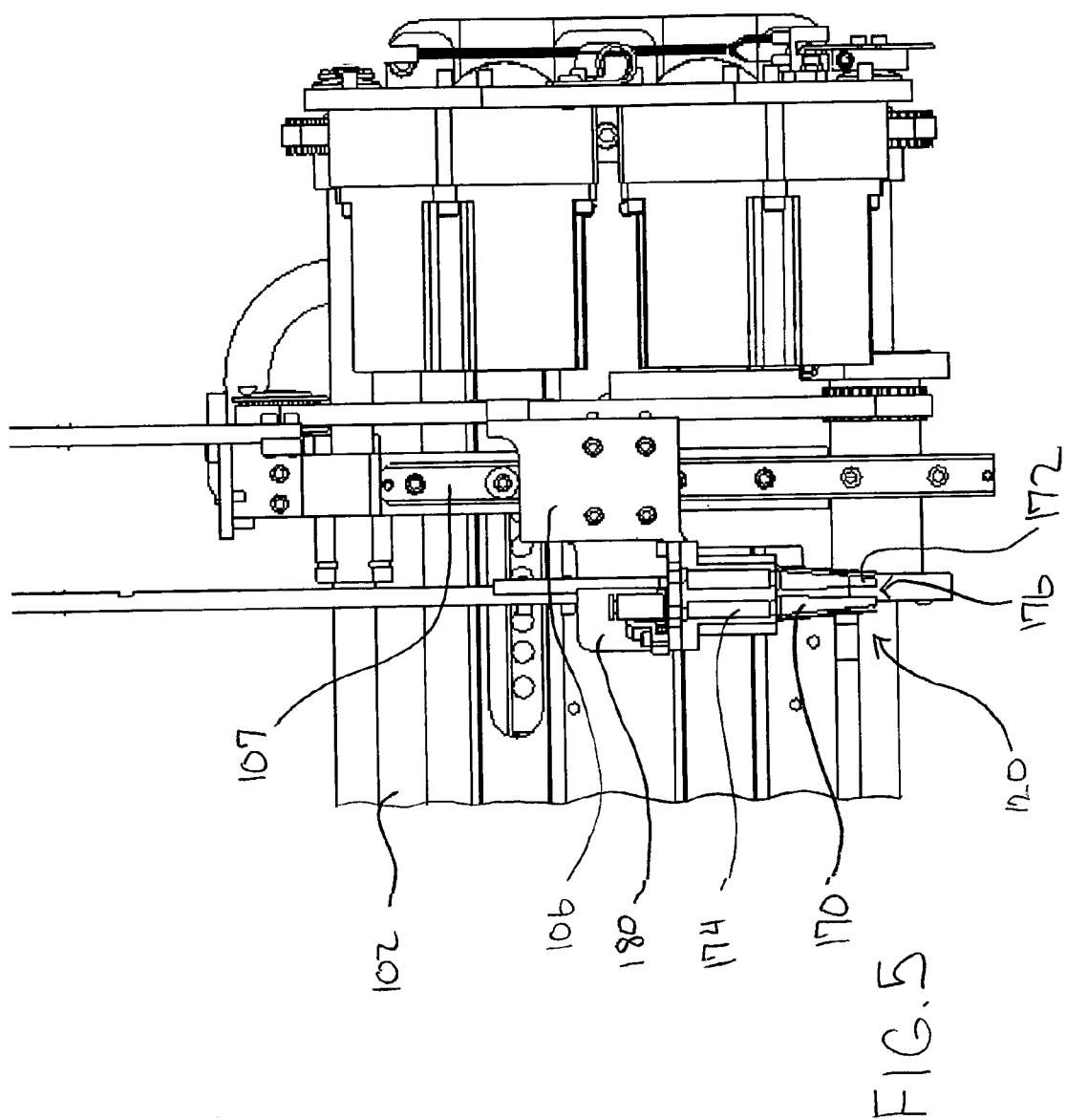
FIG. 5 shows an enlarged side view of the transport device of FIG. 4.

With reference now to FIG. 5, the transport device 120 is shown upon the end of the horizontal support 102 of the gantry robot 100. The transport device 120 is shown as a pick-and-place device that includes a gripper assembly 170 that rides upon the vertical arm 107. The gripper assembly 170 may be the same as that shown for the pick-and-place of FIG. 8. Accordingly with reference to FIGS. 5 and 8, the gripper assembly 170 includes an elongated body with a plurality of flexible spring fingers 172 connected to a cylinder 174 in a spaced apart relationship. The bottom ends of the spring fingers 172 are tapered and form a slotted circular opening 176 adapted to receive a vessel. The cylinder 174 is held by a clamp 180 which, in turn, is connected to a carriage 106 riding upon a gantry robot. A plunger 178 (see FIG. 8) moves within the cylinder 174. When the fingers 172 are forced downward onto a vessel, the spring fingers 172 spread apart and the top portion of the vessel is received through the opening 176. After passing through the opening 176, the vessel contacts the plunger 178 and forces the plunger upward relative to the fingers 172. When the plunger 178 is moved upward, an electromagnetic sensor detects its movement and the system recognizes that a vessel is within the grasp of the fingers 172. To release the vessel from the grasp of the spring fingers 172, the plunger 178 is forced downward until the top of the vessel passes through the opening 176.

Figure 6:
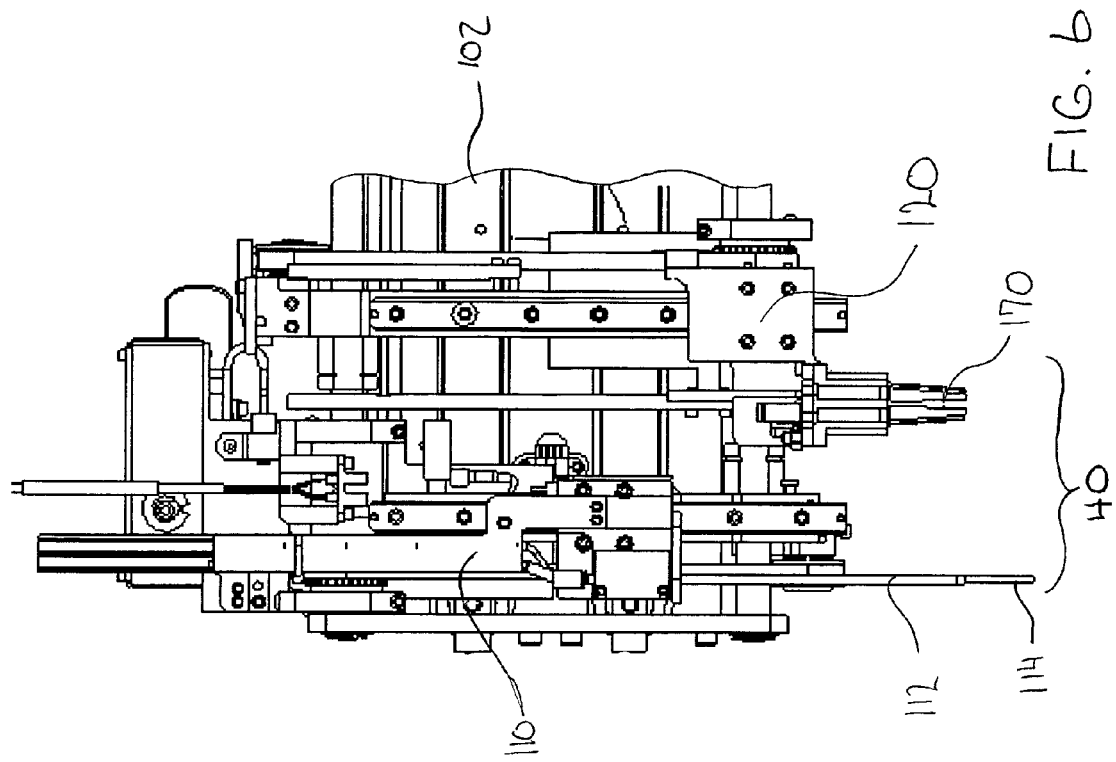
FIG. 6 shows a side view of the aspiration device and transport device of FIG. 2 positioned at a transfer station of the automated analyzer of FIG. 1.

As discussed above, both the aspiration device 110 and the transport device 120 are independently moveable along the horizontal support 102 of the gantry robot 100. Thus, as shown FIG. 6, both devices 110, 120 may be moved to one end of the horizontal support. For example, both devices 110, 120 may be moved above the transport station 40 and into position to handle or otherwise engage a primary sample container and/or the sample contained therein.

FIG. 7 shows the aspiration device 110 and the transport device 120 positioned above the sample storage unit 70 of the automated analyzer 20. The aspiration device 110 is positioned over the slot 76 in the top of the sample storage unit housing 72. This slot 76 provides access to the sample retention vessels 28 positioned within the sample storage unit 70, and allows the aspiration device 110 to deliver samples into the sample retention vessels 28 or draw samples from the sample retention vessels 28.

The transport device 120 is shown to the right of the aspiration device in FIG. 7. The transport device 120 may also be moved into position over the 76 slot in the sample storage unit housing 72 to allow the transport device 120 to interact with the sample storage unit 70. In particular, the gripper assembly 170 of the transport device 120 may deliver primary sample vessels from the transfer station 40 to the seats 29 in the wheel 74 of the sample storage unit 70. Also, the gripper assembly 170 may remove sample retention vessels 28 from the seats 29 in the wheel 74 of the sample storage unit 70. The wheel 74 of the sample storage unit 70 is rotatable with respect to both the aspiration device 110 and the transport device 120. This allows the sample storage unit 70 to move any sample retention vessel within the sample storage unit into position for interaction with the aspiration device 110 or the transport device 120 mounted on the gantry robot 100.

Additional Transport Device

With reference again to FIG. 1, the gantry robot 100 is shown intersecting with a rear transport device 150 on the automated analyzer. Transfers between the gantry robot 100 and the rear transport device occur at a secondary transport station 130. The rear transport device 150 may be any of numerous transport devices known in the art, including a shuttled carriage arrangement, a pick-and-place device, a transport belt, a robotic arm or other transport device. These and other transport devices will be known to those of skill in the art. In any event, the rear transport device 150 is configured to receive containers from the gantry robot 100, including primary sample containers 22 or sample retention containers 28, and deliver such containers to an off-board laboratory instrument 160 housed separate from the automated analyzer. After the containers are processed at the off-board instrument, they may be returned to the rear transport device 150 for delivery back to the gantry robot 100. The gantry robot may then deliver the container to the appropriate location in the automated analyzer for storage, analysis, or other processing.

In one embodiment, the off-board instrument 160 comprises a closed-tube aliquotter capable of obtaining an aliquot of a sample in a primary retention container having a cap. In this embodiment, open primary sample containers are loaded on the sample presentation unit 30 and closed sample containers are loaded at a loading station for the closed tube aliquotter. With reference to FIG. 1, closed tube sample containers loaded at the loading station 162 of the closed tube aliquotter 160 are transported into the instrument for further processing using transport device 164. After a primary sample container is loaded into the closed tube aliquotter, it is delivered to an aliquot station where the sample in the primary sample container is split into a plurality of aliquots in separate vessels. These vessels are then delivered to the automated analyzer 20 as primary sample containers. In particular, the vessels are exchanged between the automated analyzer 20 and the off-board instrument 160 at a third transfer station 140 where the rear transport device 150 of the automated analyzer interacts with the transport device of the off-board instrument 160. The rear transport device 150 accepts the vessels from the closed tube aliquotter 160 and then delivers them to the secondary transfer station 130 where the vessels may be grasped by the pick-and-place device 120 and moved on to various units within the automated analyzer 20 for further processing.

The above-described embodiment contemplates the use of different loading stations/sample presentation units for closed and open primary sample containers. However, other embodiments are contemplated where a single loading station/sample presentation unit is used to load both open and closed primary sample containers. For example, in one embodiment, the aspiration device 110 may comprise a closed tube aliquotter capable of processing both open and closed primary sample containers. In another embodiment, both open and closed primary sample containers may be loaded into the automated analyzer 20 at sample presentation unit 30 of FIG. 1. In this embodiment, when closed primary sample containers are received at the transfer station 40, the transport device 120 delivers the closed primary sample container to the secondary transfer station 130 for handling by the rear transport device 150. The rear transport device 150 then delivers the closed primary sample container to the closed tube aliquotter 160 via the third transfer station 140. As discussed above, the closed tube aliquotter 160 includes its own transport devices, such as a pick-and-place device, allowing the closed tube aliquotter to take the closed primary sample container and deliver it to an aliquot station. After the closed tube aliquotter splits the sample in the original primary sample container into a plurality of aliquots, each of the aliquots is returned to the rear transport device 150 as a subsequent primary sample container. These subsequent primary sample containers are then transferred to the gantry robot 100 for delivery to the sample storage unit, analytic unit 60, or other sample retention unit within the automated analyzer.

As set forth above, by use of the additional transport device 150, the automated analyzer 20 may be connected to an off-board laboratory instrument 160 that provides further functionality and options for the automated analyzer 20. For example, in the disclosed embodiments, the rear transport device 150 allows the automated analyzer 20 to receive and process both closed and open containers as well as containers of differing sizes.

General Operation

In operation, the automated analyzer configured to receive and process samples in a plurality of differently sized and shaped containers. Different containers may be processed differently by the automated analyzer, with some containers received into sample retention units in the automated analyzer and samples in other containers aspirated and then the containers expelled from the automated analyzer. As discussed above, when the automated analyzer is used in association with a closed tube aliquotter, both samples in both open and closed containers may also be processed by the analyzer.

With reference to FIG. 1, when using the automated analyzer 20, primary sample containers 22 having samples contained therein are first loaded into a sample presentation unit 30. The sample presentation unit 30 automatically delivers the primary sample containers 22 to the transfer station 40. An aspiration device 110 and a transport device 120 are both provided on a gantry robot 100 that operates in proximity of the transfer station 40. Accordingly, a sample within a primary sample container 22 may be aspirated from the primary sample container at the transfer station 40. Following aspiration, the aliquots of the sample are delivered to sample retention vessels at a sample retention unit within the analyzer, such as sample storage unit 70. Alternatively, instead of sample aspiration at the transfer station 40, the transport device 120 may grasp the primary sample container 22 at the transfer station 40 and deliver the entire primary sample container and its sample to a sample retention unit within the automated analyzer. For example the primary sample container 22 may be moved from the transfer station 40 to the sample storage unit 70 as one of the plurality of sample retention vessels held within the sample storage unit 70.

In any event, after a sample is moved from the transfer station 40 by aspiration or movement of the primary sample container, the sample is further processed by the automated analyzer. The further processing may include, for example sample storage, sample analysis, mixing the sample with a reagent, or other sample processing.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A method of preparing samples for analysis, using an automated analyzer including a transfer station, a sample presentation unit coupled to the transfer station and configured to receive a plurality of primary sample containers, and a sample storage unit and an analytic unit coupled to the transfer station and configured to receive a plurality of sample retention vessels, wherein the analytic unit is configured to receive and analyze samples, the method comprising:
    a) loading the plurality of primary sample containers into a presentation section of the sample presentation unit, each of the plurality of primary sample containers containing a sample, and then transferring the plurality of primary sample containers to the transfer station from the presentation section;
    b) transferring a first primary sample container of the plurality of primary sample containers at the transfer station into the sample storage unit or the analytic unit, and if the first primary sample container is transferred to the sample storage unit, then the first primary sample container is thereafter transferred to the analytic unit;
    c) aliquoting the sample from a second primary sample container of the plurality of primary sample containers at the transfer station into at least one of the plurality of sample retention vessels in the sample storage unit or the analytic unit, and if the sample is aliquoted into the at least one of the plurality of sample retention vessels in the sample storage unit, the at least one of the plurality of sample retention vessels is thereafter sent to the analytic unit; and
    d) processing the sample in the first primary sample container and the sample aliquoted from the second primary sample container.

2. The method of claim 1 wherein processing the sample in the first primary sample container comprises removing an aliquot of the sample in the first primary sample container.

3. The method of claim 1 wherein processing the sample from the second primary sample container comprises analyzing the sample from the second primary sample container.

4. The method of claim 1 wherein loading the plurality of primary sample containers comprises manually loading the plurality of primary sample containers into the presentation section of the sample presentation unit and automatically delivering the plurality of primary sample containers to the transfer station.

5. The method of claim 1 wherein loading the plurality of primary sample containers comprises receiving at least some of the plurality of primary sample containers from a laboratory instrument housed separate from the automated analyzer.

6. The method of claim 5 wherein the laboratory instrument comprises a closed tube aliquotter.

7. The method of claim 6 wherein loading the plurality of primary sample containers comprises delivering a third primary sample container of the plurality of primary sample containers from the automated analyzer to the closed tube aliquotter and receiving the at least some of the plurality of primary sample containers from the closed tube aliquotter, each of the at least some of the plurality of primary sample containers comprising an aliquot of the sample in the third primary sample container.

8. The method of claim 1 wherein the automated analyzer comprises:
    a transport device configured to transfer the first primary sample container to the sample storage unit; and
    an aspiration device configured to transfer the sample from the second primary sample container into the at least one of the plurality of sample retention vessels in the sample storage unit.

9. The method of claim 8 wherein the transport device is a first transport device and wherein the automated analyzer comprises a second transport device separated from the transfer station and is configured to receive primary sample containers from the first transport device.

10. The method of claim 8 wherein the transport device is a first transport device and wherein the automated analyzer comprises a second transport device configured to deliver primary sample containers to the first transport device.

11. The method of claim 10 wherein the second transport device is further configured to deliver primary sample containers from a laboratory instrument housed separate from the automated analyzer.

12. The method of claim 11 wherein the second transport device is further configured to receive primary sample containers from the laboratory instrument housed separate from the automated analyzer.

13. The method of claim 8 wherein the transport device is part of a gantry robot.

14. The method of claim 1 wherein the analytic unit includes at least one of an incubator station, a wash station, and a read station.

15. The method of claim 1 wherein the analytic unit comprises an immunoassay system.

16. The method of claim 1 wherein the automated analyzer is configured to process differently sized and shaped containers.

* * * * *